United States Patent
du Preez et al.

(10) Patent No.: US 12,387,845 B2
(45) Date of Patent: Aug. 12, 2025

(54) HEALTH MANAGEMENT THROUGH CAUSAL RELATIONSHIP BASED FEEDBACK ON BEHAVIOR AND HEALTH METRICS CAPTURED BY IOT

(71) Applicant: LifeQ B.V., Amsterdam (NL)

(72) Inventors: Franco Bauer du Preez, Cumming, GA (US); Jacobus Barend van Dyk, Malmesbury (ZA); Laurence Olivier, Alpharetta, GA (US)

(73) Assignee: LIFEQ B.V., Amsterdam (NL)

( * ) Notice: Subject to any disclaimer, the term of this patent is extended or adjusted under 35 U.S.C. 154(b) by 121 days.

(21) Appl. No.: 18/553,419

(22) PCT Filed: Mar. 29, 2022

(86) PCT No.: PCT/US2022/022281
§ 371 (c)(1),
(2) Date: Sep. 29, 2023

(87) PCT Pub. No.: WO2022/212324
PCT Pub. Date: Oct. 6, 2022

(65) Prior Publication Data
US 2024/0194346 A1    Jun. 13, 2024

Related U.S. Application Data

(60) Provisional application No. 63/167,361, filed on Mar. 29, 2021.

(51) Int. Cl.
*G16H 50/20* (2018.01)
*G16H 20/00* (2018.01)
(Continued)

(52) U.S. Cl.
CPC ............. *G16H 50/20* (2018.01); *G16H 20/00* (2018.01); *G16H 40/67* (2018.01); *G16H 50/30* (2018.01); *G16H 50/70* (2018.01)

(58) Field of Classification Search
CPC ...................................................... G16H 40/67
See application file for complete search history.

(56) References Cited

U.S. PATENT DOCUMENTS

| | | | |
|---|---|---|---|
| 10,252,145 B2 | 4/2019 | Tran et al. | |
| 2016/0217266 A1* | 7/2016 | Damani | G16H 40/67 |

(Continued)

OTHER PUBLICATIONS

The International Search Report/Written Opinion released in the parent application PCT/US2022/022281 on Jun. 30, 2022; 11 pages.

(Continued)

*Primary Examiner* — Joseph D Burgess
(74) *Attorney, Agent, or Firm* — Smith Gambrell & Russell LLP

(57) ABSTRACT

A method, and, system for modeling causal intra-individual relationships between behavioral patterns and health metrics and recommending changes in behavior that will optimize health as measured by IOT technology. The method and system may at times implement a learning mode (exploration) to identify true causal relationships between behaviors and health metrics and may at other times implement an optimization or exploitation mode for improving on the existing causal relationships between behaviors and health metrics. The method and system may give a user feedback to improve health metrics by changing behaviors and may further comprise measuring and storing behavioral and health data, establishing models taking as input the behavioral data and forecasting an expectation of the health data for an individual as a result.

19 Claims, 5 Drawing Sheets

(51) Int. Cl.
*G16H 40/67* (2018.01)
*G16H 50/30* (2018.01)
*G16H 50/70* (2018.01)

(56) References Cited

U.S. PATENT DOCUMENTS

| | | |
|---|---|---|
| 2017/0000422 A1 | 1/2017 | Sai et al. |
| 2017/0329933 A1 | 11/2017 | Brust et al. |
| 2017/0347899 A1 | 12/2017 | Bhushan et al. |
| 2018/0001184 A1 | 1/2018 | Bao et al. |
| 2018/0342323 A1 | 11/2018 | Shankar et al. |
| 2019/0087954 A1 | 3/2019 | Lloyd et al. |
| 2019/0189025 A1* | 6/2019 | Angelopoulos ........ G16H 20/10 |
| 2019/0244714 A1 | 8/2019 | Morra et al. |
| 2020/0367801 A1 | 11/2020 | Yassine et al. |

OTHER PUBLICATIONS

Nag, Nitish, "Health State Estimation", Dissertation—University of California Irvine, Mar. 16, 2020; 308 pages.
Extended European Search Report released by the European Patent Office on Apr. 25, 2025 for corresponding European Patent Application No. 22 78 1997; 15 pages.

* cited by examiner

HEALTH MANAGEMENT THROUGH CAUSAL RELATIONSHIP BASED FEEDBACK ON BEHAVIOR AND HEALTH METRICS CAPTURED BY IOT

BACKGROUND OF THE INVENTION

With advances in the measurement of health parameters through the use of wearable- and/or nearable devices, the need and ability to establish relationships between an individual's behavior and their overall health has increased significantly. Since the behavioral patterns of an individual have both acute as well as long lasting effects on their health, there is an interest in identifying healthy and unhealthy behaviors and augmenting/modifying these behaviors to optimize health. Establishing relationships between behavioral factors as input values and health metrics as output values is done by applying modeling practices to identify and quantify the impact that certain behaviors have on health. However, the current state of the art of modeling health, wellness and medicine (HWM) is heavily reliant on establishing population level correlations between input values and output values as illustrated in the guidelines of the Physical Activity Guidelines (PAG) advisory committee and the World Health organization (WHO) on physical activity. This information is based on the association between self-reported activity levels and all-cause mortality at a population level. Causative studies on the relationships between behavioral factors such as, but not limited to, exercise and sleep on health, have not been explored or employed. Therefore, there is a need to explore and employ such studies. Further, within the field of applied HWM models, there is a clear lack of personalization and reliable predictions of how much a specific individual's behavior causes positive or negative health impacts. Therefore, there is a need to determine how the individual behavior of an individual impacts that individual's health, and develop models in such areas.

Within the field of modeling HWM, the approaches used to identify and quantify relationships between behaviors and health vary significantly in both application and complexity. These approaches may be categorized into different subsections, differing in approach, complexity and quantifiability. An example of the most basic forms of modeling HWM may be to establish a relationship between dietary practices (as a behavioral factor) and weight (as a health factor) using data from a population study where there is one data point of self-reported dietary practice and one data point of weight change over a study period per participant. The dietary practice average, in this example, would be one value each for the average daily amounts of fats, proteins, carbohydrates and fiber that the participant consumed throughout the study period and health would be one value for the weight change over the period (kilograms lost or gained). Within this example, there is little regard for different requirements based on personalization and all information in a predictive model trained on dietary practice and weight change would rely on comparisons between individuals rather than comparisons regarding an individual, that is information on how an individual's health responds over time to a behavioral intervention. For instance, the carbohydrate requirements of an avid exerciser may be significantly higher in comparison to an individual that does little to no exercise. Moreover, the dietary requirements of an individual may change as the fitness level and exercise regime of the individual changes and thereby requiring different recommendations at different timepoints for the same individual.

Furthermore, the distinction between inter-individual modeling practices and intra-individual modeling practices can be highlighted. Inter-individual modeling practices regard all individuals or groups of individuals, such as all males, all children, all athletes etc., as having the same physiology and that behavioral factors have the same impact on their health metrics which may be exemplified by using population-based modeling practices. In contrast, intra-individual modeling practices consider each individual as separate from the population and as having a unique set of physiological parameters and unique behaviors that may impact their physiology uniquely.

Therefore, there is a need for improving personalized health by establishing causal, intra-individual relationships between behaviors and health metrics and a system for applying these relationships to inform users of these relationships and recommend to users how augmentation or modification of their behaviors may improve their health.

SUMMARY OF THE INVENTION

Embodiments of the claimed invention entail methods for establishing a causal intra-individual relationship between behavioral factors and health metrics. The behavioral factors can include, but are not limited to, sleep, exercise, dietary regime and medication use measured through the use of motion sensor(s) embedded into wearable and/or nearable devices or through self-reporting by the user or a third party. These health metrics can include, but are not limited to, resting heart rate, heart rate variability, pulse waveform, pulse wave velocity, augmentation index, resting breathing rate, breathing volume, cough frequency and VO2max. These causal intra-individual relationships may be modeled for the purposes of identifying causal relationships between behaviors and health metrics, quantifying these relationships and communicating how modification of specific behavioral factors may improve health metrics and the overall health of individuals. Furthermore, recommendations to the modification of behaviors may be deduced by the system and communicated through to the user. The ability to identify, quantify and communicate causal intra-individual relationships between behavioral practices and health metrics, and the ability to identify and recommend how augmentation and/or modification of behavioral practices will impact health is a significant improvement over the current methods of relating behavior to health with significant benefits to users for improving health.

In an aspect, the invention is directed towards a method for improved health management using an IoT setup of interconnected electronic devices and sensors that includes measuring and storing behavioral data and health data of a plurality of users, analyzing the health data of the plurality of users to establish informative outcomes, generating health metrics from the health data, establishing a relationship between the informative outcomes and the health metrics, identifying and quantifying a causal relationship between the behavioral data and the health data from a behavior time window and from a health data time window, wherein the beginning of the behavior time window precedes the beginning of the health data time window, to derive behavioral recommendations, providing the derived behavioral recommendations to one of the plurality of users or to a third party, and investigating changes to the information that was sent to the third party to influence user behavior optimally. The method can include investigating changes to the information that was sent to third parties to influence end-user behavior optimally.

In such aspects, the behavioral data can include one of sleep parameters (e.g., total sleep time, bedtime variability or wake-up time variability), exercise parameters (e.g., intensity minutes, event duration or event type), dietary regime (e.g. amounts of proteins, fats, carbohydrates or fiber), or medication usage (e.g., glucose management, blood pressure medication or antidepressant use). Further, the health data can include at least one of cardiovascular metrics (e.g., resting heart rate, pulse waveform, heart rate variability or pulse wave velocity), respiratory metrics (e.g., resting breathing rate, breathing volume or cough frequency), or oxygen saturation (e.g., VO2max measurements). The informative outcomes can include vitality (e.g., risk of all cause mortality, risk of developing cardiovascular diseases, life expectancy, biological age or years left to live), respiratory health (e.g., risk of developing chronic respiratory diseases); or fitness level (e.g., fitness scoring and recovery time after fitness events).

In an aspect, the behavioral data can be measured by sensors including, but not limited to, accelerometers, inertial gyroscopes, stop-motion sensors, or Micro Electro Mechanical Systems (MEMS) embedded in wearable devices or nearable devices. The health metrics can be measured using physiological signal sensors including, but not limited to, heart rate sensors, PPG sensors, oximetry sensors, electro-dermal activity (EDA), galvanic skin response (GSR), or ECG sensors embedded in wearable or nearable devices.

In an aspect, the causal relationship between behavioral and health data is established by using machine learning to derive models to describe the causal relationship between behavioral and health data, communicating this relationship to the user for the purpose of illustrating the impact of their behaviors on their health, calculating the optimal behavioral changes through deriving an optimal decision policy and recommending changes to the user's behavior either through making randomized changes to behaviors when operating in exploration mode, or through recommending the changes in behavior based on the current decision policy when operating in exploitation mode, using reinforcement learning techniques to evaluate whether the behavior feedback to the user is randomized for the purpose of generating more data for learning, or whether the behavior feedback to the user is optimal to improve the health of the user, and motivating the user to modify the user's behaviors for the purpose of improving the user's health and wellbeing. In such aspects, the machine learning includes using linear regression, logistic regression, least squares fit modeling, decision tree modeling, unsupervised machine learning, or supervised machine learning approaches to model the causal relationship between the behavioral data and the health data.

In an aspect, a specific time window size is used to discover causative or potentially causative relationships between behavioral factors and health metrics and where those relationships are then extrapolated to smaller time durations, such as a single day, to provide increasingly more immediate feedback to the user, for the purpose of effecting behavioral change as the cause and effect relationship is still fresh in the mind of the user. In other aspects, the time window of behavioral data and the time window of health data comprise adjacent and non-overlapping time windows or comprise limited-overlapping time windows, and wherein the behavioral data and the health data are used to discover causative relationships between behavioral factors and health metrics where the start of the behavioral data time window precedes the start of the health data time window and where a causal relationship comprises utilizing a Granger causality test.

In an aspect, the method of the current invention utilizes reinforcement learning with Q-learning and E switching to control when exploration and when exploitation are performed by the system. In such aspects, the exploration can include learning through randomized changes in recommended behavior and the exploration comprises applying an optimized decision policy. In an aspect, deriving recommendations includes Q-learning to derive an optimal decision policy of recommendations of behaviors for feedback to the user. In other aspects, the method, when an $\varepsilon$-greedy parameter is greater than or equal to a predefined threshold, can operate in the exploration mode, where randomized recommendations are given to the user as feedback, and when the $\varepsilon$-greedy parameter is lesser than a predefined threshold, operating in the exploitation mode, where the optimal decision policy, derived through Q-learning is recommended to the user. The $\varepsilon$-greedy parameter can switch dependent on the accuracy of the model describing the causal relationship between behavioral and health data, wherein the model will operate more in exploration mode if a statistically significant causal relationship is not obtained, and the model will operate more in exploitation mode if a statistically significant causal relationship is obtained.

The system can request the user to perform behavioral changes, which may further comprise manual confirmation, or which may further comprise automatic detection in the behavioral data, and which are randomized when operating in exploration mode, and which are based on an optimized decision policy, when operating in exploitation mode. Further, the relationship between the behavioral data and the health data can be tested and refined by randomizing the behavior recommendations made by the method and, wherein an effect of this randomization is monitored statistically to improve the model.

In an aspect, feedback can be provided to the user via a user communication interface comprising a smart watch display, cellular applications, cellular messaging, cellular calls or web based programs. The feedback may include recommendations of behaviors for the user to complete including daily or weekly goals, and the recommended behaviors are those behaviors with the largest causal relationship between behavioral data and health data. Changes to a behavioral program can be made such as to omit or reduce recommendations on behavior as well as feedback to the user to quantify the overall causal effect of the IOT intervention system in bringing about changes in health metrics, and the data may be aggregated over multiple users to prove causal effects on health by introducing the system to a population. Behavioral suggestion changes may be reduced or removed for the purposes of AB testing, or within a control group to evaluate quantitatively the impact of the system as a whole on population health.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and the invention may admit to other equally effective embodiments.

Figure 1:
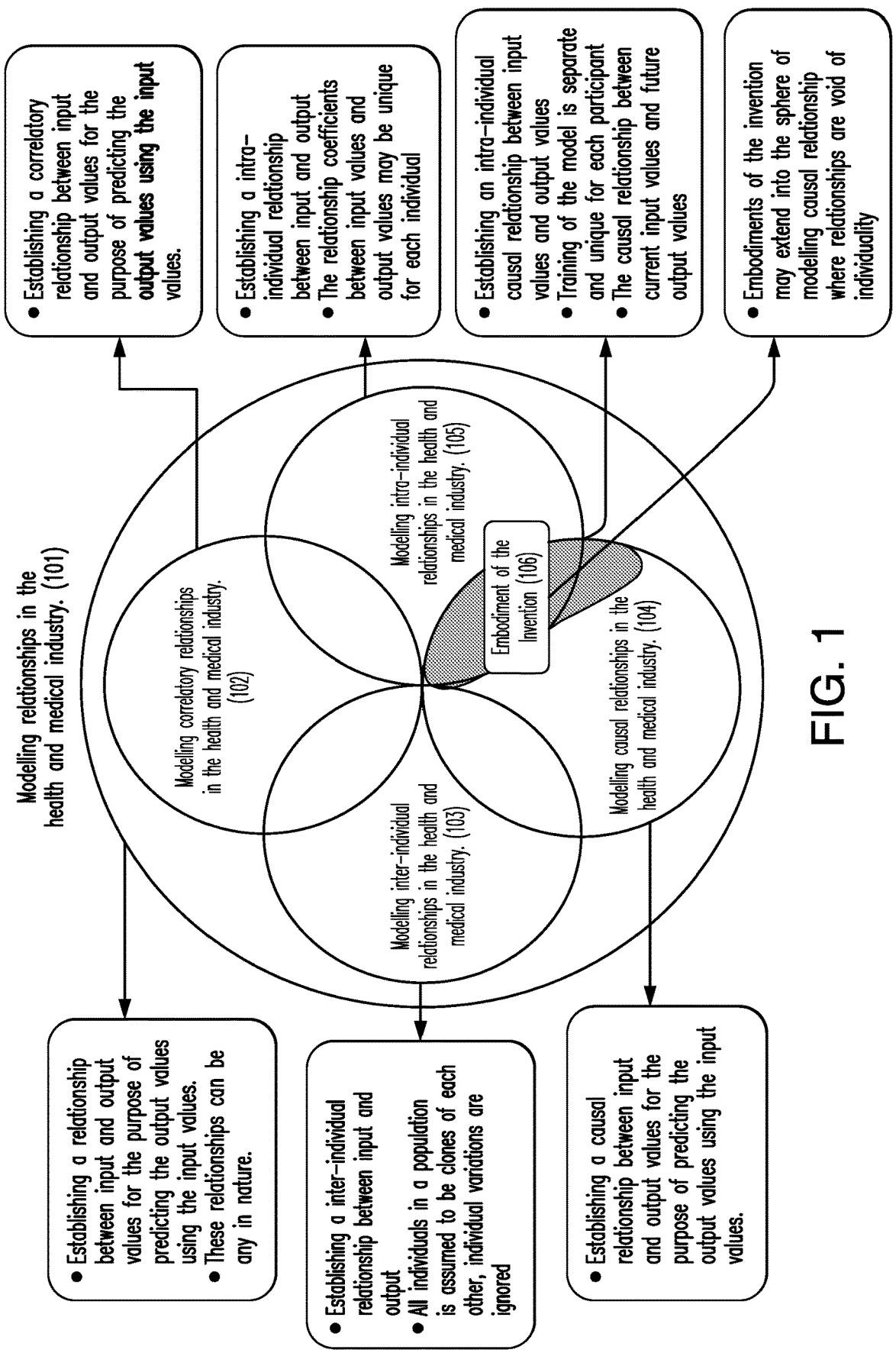
FIG. 1 is a schematic illustration of modeling relationships between input and output values within the personalized health and medical industries according to an aspect of the present invention.

Other features of the present embodiments will be apparent from the Detailed Description that follows.

Definitions

PPG—Photoplethysmography
ECG—Electrocardiogram
NMR—Nuclear Magnetic Resonance
MRI—Magnetic Resonance Imaging
EDA—Electrodermal activity
GSR—Galvanic skin response
Wearable device—A device that is worn on and/or attached to the body for the purposes of body monitoring
Nearable device—A device placed near the body for the purposes of body monitoring
Body Monitoring—The use of sensors placed on and/or close to the individual's body such as, but not limited to wrist worn PPG devices, pulse oximeter, ECG, and further includes, but are not limited to, hypothetical NMR/MRI wearable or nearable devices which may exist in future.
Health Metrics—Physiological parameters
IOT—Internet of things

DETAILED DESCRIPTION

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the disclosure. Rather the scope of the disclosure is defined only in accordance with the following claims and their equivalence. The following detailed description of the exemplary embodiments will so fully reveal the general nature of the disclosure that others can, by applying knowledge of those skilled in the relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

The present invention here describes the evaluation of behavioral factors or behavioral data, or deductions made from such data, obtained about an individual through the use of wearable and/or nearable devices and/or through manual input by the user and establishing a causal relationship to health metrics obtained from wearable and/or nearable devices, through the use of modeling practices such as, but not limited to, linear regression, least squares fit modeling, and decision tree modeling as well as unsupervised, and, more typically, supervised machine learning approaches such as, but not limited to, neural networks, support vector machines, and support vector regression.

The content disclosed in the detailed description will first discuss the approach that the invention uses to improve personalized health management and how it differs from general practice. Second, how data is acquired will be described and how it is stored into multiple data streams through utilization of an IOT setup. Third, the detailed description will outline how these multiple data streams will be utilized by the invention for deriving and quantifying causal relationships between behavioral data streams and health metric data streams. The methods used by the invention for deriving and quantifying these causal relationships will be discussed along with relevant exemplary embodiments to better illustrate the invention. The methods used by the invention will be discussed systematically and it will be illustrated how these methods become more complex and are required to derive causal relationships between behavioral data and health metrics. Lastly, the detailed description will discuss how user feedback may be relayed to the user and the intended impact this may have on the health of the user.

Present Invention vs. Standard Practice

The embodiment of the invention differs from the embodiment of general modeling practices within the health monitoring field by explicitly investigating intra-individual causal relationships between behavioral factors and health metrics with the explicit goal of establishing a causal relationship between behaviors and health to better recommend modifications of behavior to users. In an aspect, the invention may act as a personal trainer that may recommend changes in a user's behavior with the aim of optimizing the health of the user. This differs from general practice which is aimed at establishing relationships such as associative relationships between behavioral factors and health metrics and delivering feedback of "bad behaviors" to the user. The embodiment of the invention is concerned with establishing a causal link between behaviors and health, rather than merely observing that a specific behavior is associated with a specific health state. Furthermore, general modeling practices typically focus on population-based, inter-individual relationships between behavioral factors and health metrics as is illustrated by the guidelines of the Physical Activity Guidelines (PAG) committee and the World Health Organization (WHO) on physical activity, which is reliant on the association between self-reported activity levels and all-cause mortality. The systems and methods of the present invention focus on a section of potential modeling practices within the health monitoring field pertaining to causal intra-individual relationships between behaviors and health metrics, as illustrated in FIG. 1. Moreover, according to one aspect of the current invention, causal relationships between behavioral factors and health metrics on an intra-individual level are derived, where the causal relationship is explicitly and continuously trained for each participant individually, using available longitudinal data obtained by constant data collection through body monitoring of the user over an extended period of time.

As shown in FIG. 1, the field of modeling in personalized health and medicine focuses on establishing relationships of any nature between input and output values for the purpose of predicting output values using data available on input values. FIG. 1 illustrates the modeling of relationships between input and output values within the personalized health and medical industries (101). Within this broader field, various modeling techniques are employed. Of interest here is the relation between inter-individual modeling techniques (103), focused on establishing relationships between input values and output values within a specific population (all individuals are treated as clones), and intra-individual modeling techniques (105), focused on establishing relationships between input values and output values with a specific individual, resulting in unique solutions for each individual. Furthermore, the relation between establishing correlative relationships (102), where input values and output values have a statistically significant correlation with one another without any causal relationship between input and output values, and causal relationships (104), where a clear cause and effect relationship exists between input values (cause) and output values (effect). Modeling relationships in the health and medical industry (101) entails establishing any associative relationship (of any nature) between input values and output values for the purposes of predicting output values using the input values. There are several subcategories within this field with regards to approaching and modeling practices. The modeling of correlatory relationships (102) pertains to deducing statistically significant relationships between input values and output values and using these statistically significant relationships to make predictions. In contrast, the modeling of causal relationships (104) rely on specifically identifying which behaviors cause what changes in health metrics.

The modeling of inter-individual relationships (103) typically pertains to population based studies in which the physiology of all individuals, or groups of individuals, e.g. all males, all children, all athletes, are assumed to be the same. In contrast, modeling intra-individual relationships (105) pertains to viewing the physiology of each individual as unique and separate from other individuals. Therefore, the relationship coefficients relating input values to output values are determined for each individual separately. The embodiment of the invention (106) illustrated in FIG. 1 pertains to the overlap of the two methodologies of intra-individual and causal relationships, and establishes a method for modeling causal intra-individual relationships, by training the model separately for each individual and deriving unique solutions for predicting health metrics in each individuals.

Figure 2:
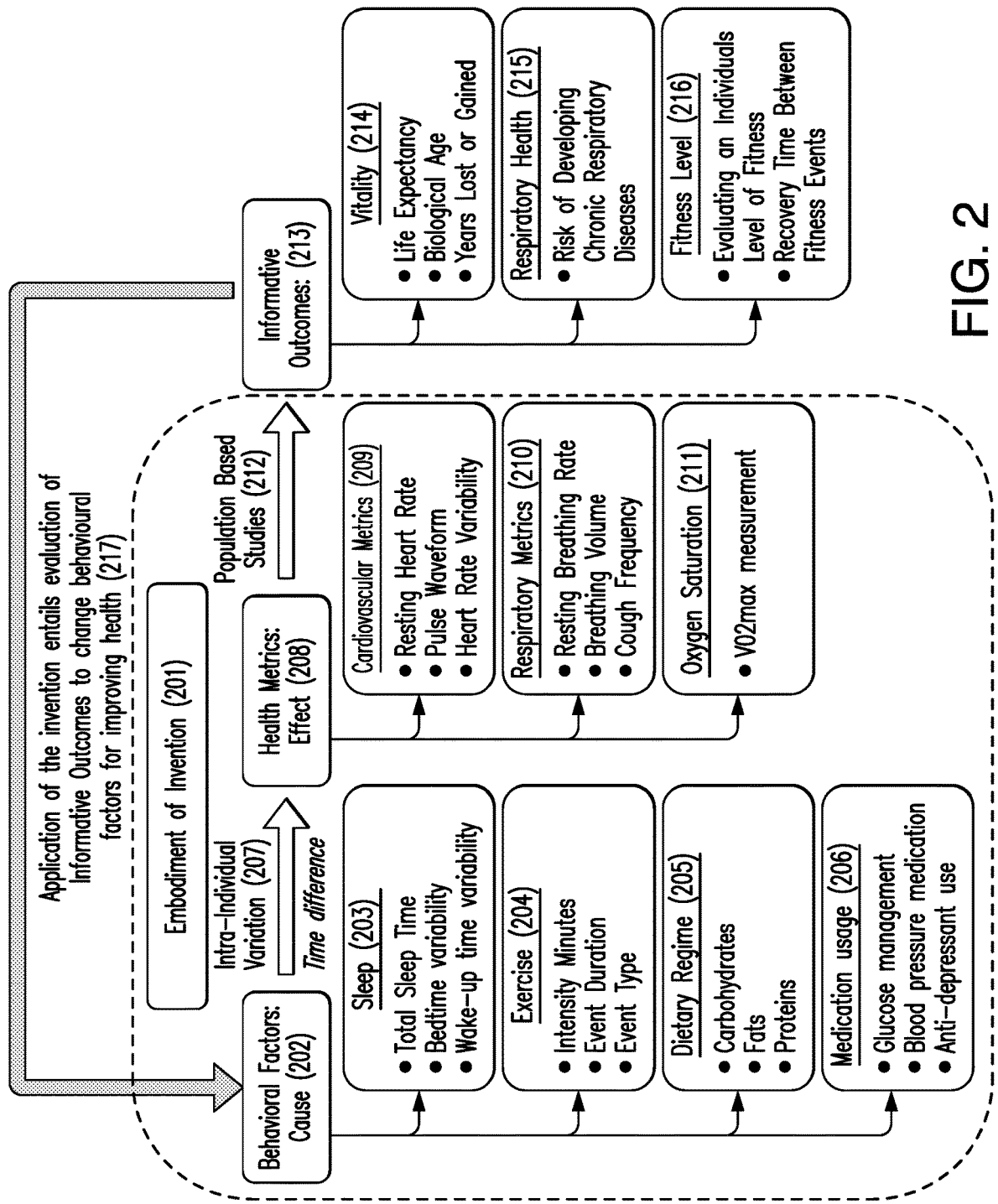
FIG. 2 is a schematic illustration of a method to determine relationships between various behavioral factors, health metrics, and informative outcomes according to an aspect of the present invention.

FIG. 2 illustrates a method (201) to determine relationships between behavioral factors (202) (such as, but not limited to sleep (203), exercise (204), dietary regime (205) and medication use (206)), health metrics (208) (such as, but not limited to cardiovascular metrics (209), respiratory metrics (210) and oxygen saturation (211)), and informative outcomes (213) (such as, but not limited to vitality (214), respiratory health (215) and fitness level (216)), according to an aspect of the present invention. The method (201) pertains to identifying and quantifying a causal intra-individual relationship (207) between behavioral factors (202) and health metrics (208). There is a time separation between the behavioral input values (202) and the health output values (208). FIG. 2 also illustrates the pre-required relationship (212) between health metrics (208) and informative outcomes (213) for establishing the criteria of healthy vs. unhealthy states for health metrics, which may be derived through population-based studies and/or from literature such as the Framingham study relating health metrics to the risk of developing cardiovascular disease or an analysis relating resting heart rate in the general population to all-cause mortality (Zhang D, Shen X, Qi X. Resting heart rate and all-cause and cardiovascular mortality in the general population: a meta-analysis. *CMAJ*. 2016; 188(3):E53-E63. doi: 101503/cmaj.150535). Furthermore, the feedback relationship (217) between informative outcomes (213) and behavioral factors (202) is shown. In an aspect, the method (201) allows for establishing a relationship between behavioral factors and informative outcomes and therefore, allows for augmentation and modification of behavioral factors (202) to improve health.

The behavioral data may include, but are not limited to sleep parameters such as, but not limited to total sleep time, time-to-bed, time-to-wake-up, sleep movements, awakening events and duration of sleep cycles, and exercise parameters such as, but not limited to fitness duration, intensity minutes and number-of-fitness-events, whereas the health metrics may include, but are not limited to, heart rate, breathing rate, cough frequency, VO2max, blood pressure and genetic profile. In an aspect, the behavioral data and health metrics may be obtained through body monitoring or through obtaining publicly disclosed information, such as but not limited to genetic profile, obtained through web based searches, or by disclosure from third party genetic profiling companies under the consent of the user. Furthermore, additional information such as, but not limited to age, gender, body mass, height, current or historical smoking status, alcohol consumption and skinfold measurements, which require manual measurement and/or verbal or written input may be manually entered onto the device and/or cloud-based platform.

Collecting the Data

Figure 5:
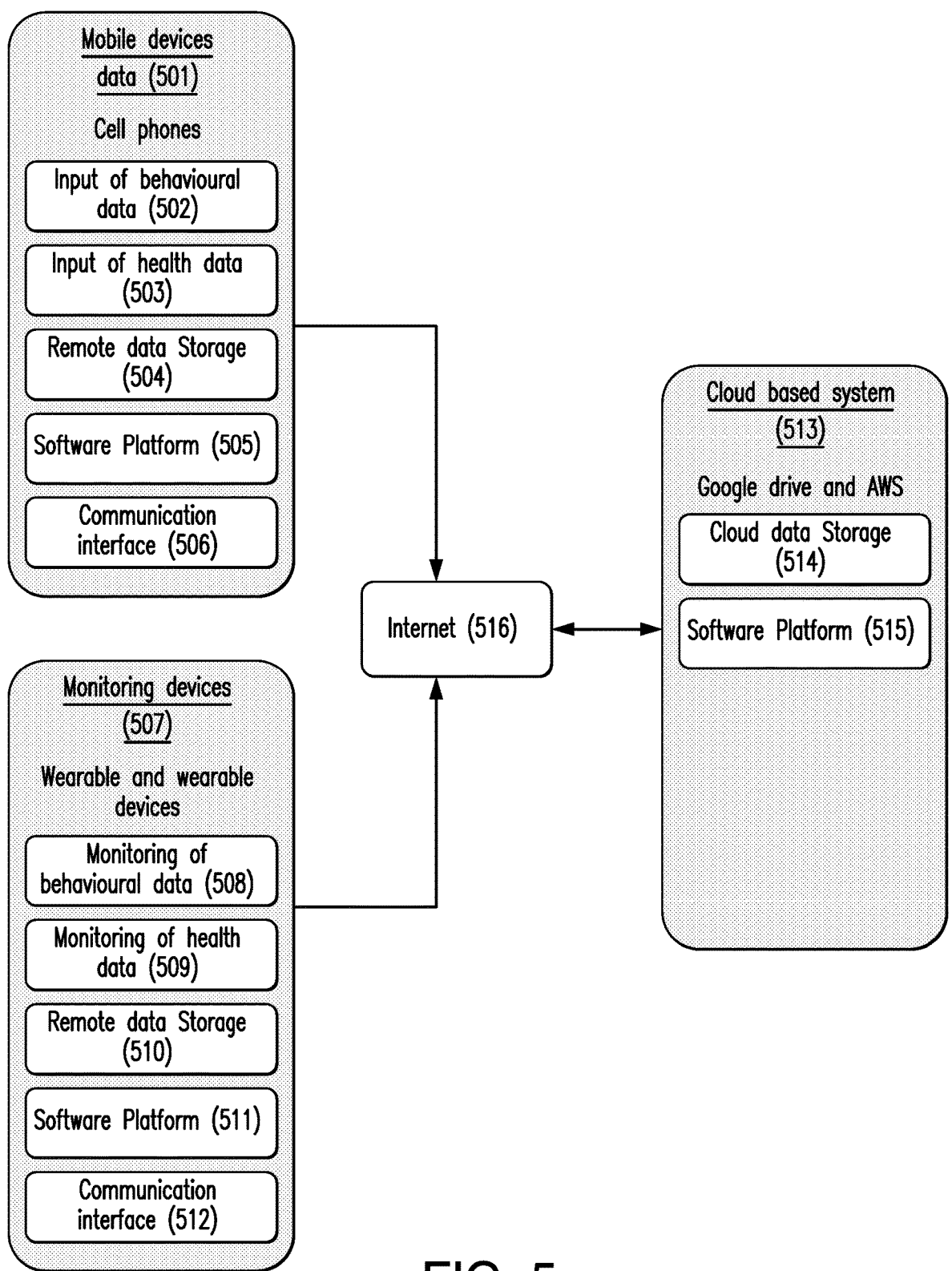
FIG. 5 is an illustration of the Internet Of Things (IOT) setup used for the embodiment of the invention.

In an aspect, behavioral data pertaining to lifestyle factors and/or the health metrics of a specific individual may be obtained through the use of sensors placed on (wearables) and/or close (nearables) to the individual's body such as, but not limited to wrist worn PPG devices, pulse oximeter, ECG, accelerometers, EDA, GSR, inertial gyroscopes, stop-motion sensors, MEMS (Micro Electro Mechanical Systems) devices and further includes, but are not limited to, hypothetical NMR/MRI and Raman spectroscopic wearable and/or nearable devices which may exist in future, referred to in this document as body monitoring. The behavioral data and/or health metrics obtained from body monitoring may be continuously collected from a range of supported body monitoring devices and digitized into longitudinal data streams and recorded as part of the Internet Of Things (IOT) setup used for implementation of the invention, as shown in FIG. 5 and discussed in detail below. The IOT refers to the interconnectivity of "things" embedded with sensors, software and other technologies, such as, but not limited to wearable devices, nearable devices, cellular communication devices, cloud-based computing platforms and remote computing platforms through the use of the internet for the purpose of data storage, data transfer and data modification.

Figure 3:
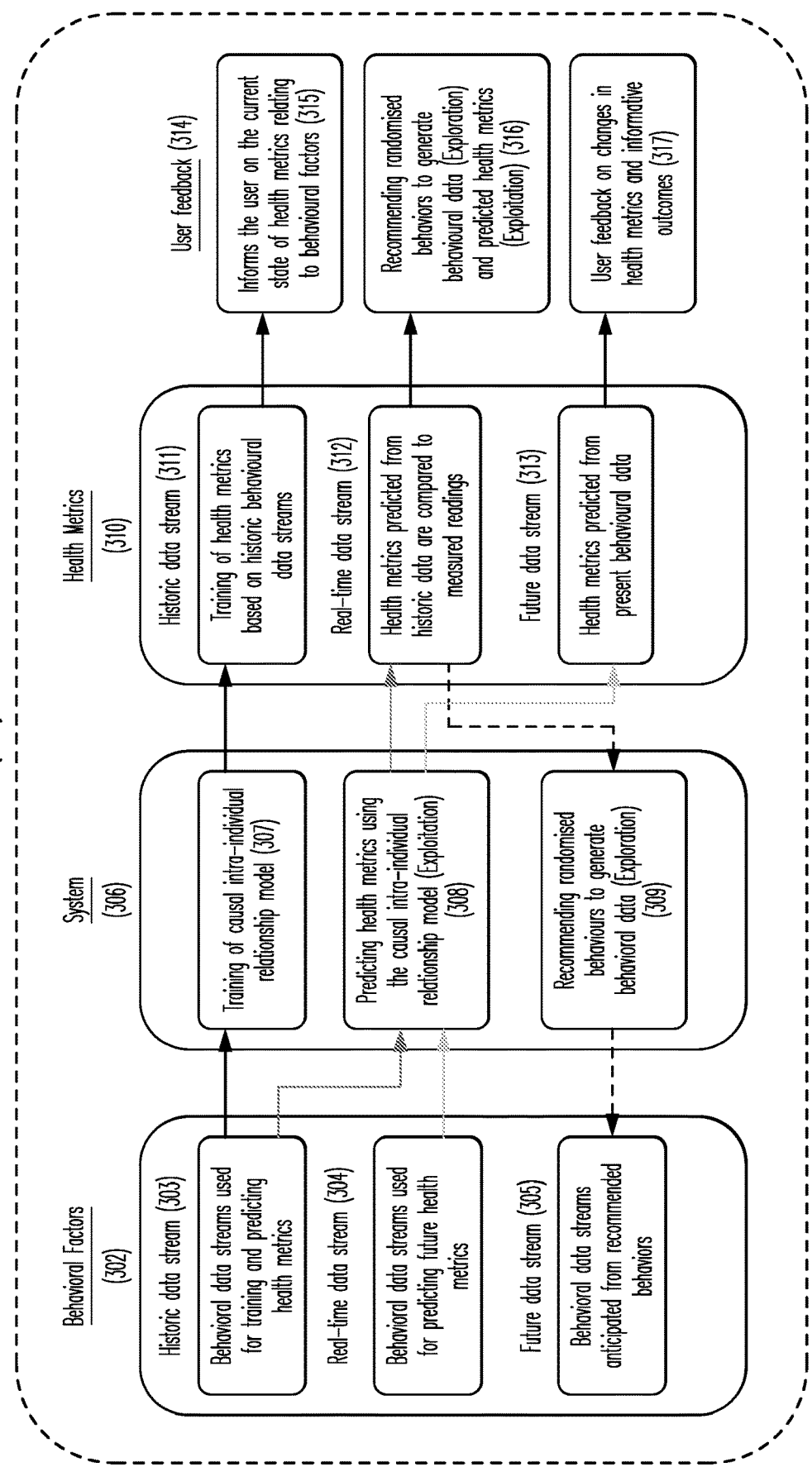
FIG. 3 is a schematic representation of a method according to an aspect of the present invention.

The method (301), as shown in FIG. 3, records data from behavioral factors (302) as historic (303), real-time (304) and future data streams (305), which may be monitored through body monitoring devices such as, but not limited to wearable and/or nearable devices. Similarly, health metrics (310) are recorded as historic (311), real-time (312) and future data streams (313), which may be monitored through body monitoring devices such as, but not limited to wearable and/or nearable devices. FIG. 3 also illustrates how the system (306) interacts with these data streams. The system (306) is set up to model causal intra-individual relationships and train these models (307) using historic behavioral data streams (303). The system makes predictions (308) of real-time (312) and future health metrics (313) based on historic (303) and real-time behavioral data streams (304) respectively. Furthermore, the system may recommend randomized behaviors (309) to the users for the purpose of generating future behavioral data streams (305) as training data for the system. FIG. 3 illustrates the type of feedback that may be given to the user (314). User feedback entails informing the user on the current relationship between their behavioral factors and their health metrics (315) as derived from historic data streams. Randomized recommendations to perform specific behaviors may be made to the user to generate behavioral data for the purpose of training and improving the model (exploration), as well as predicting health metrics based on the current understanding of the model (exploitation) (316). Furthermore, the user may be informed on how the changes they made in behavioral factors may benefit their health metrics and informative outcomes in the future, through making predictions (317).

Deriving Causal Relationships Between the Data Streams

Figure 4:
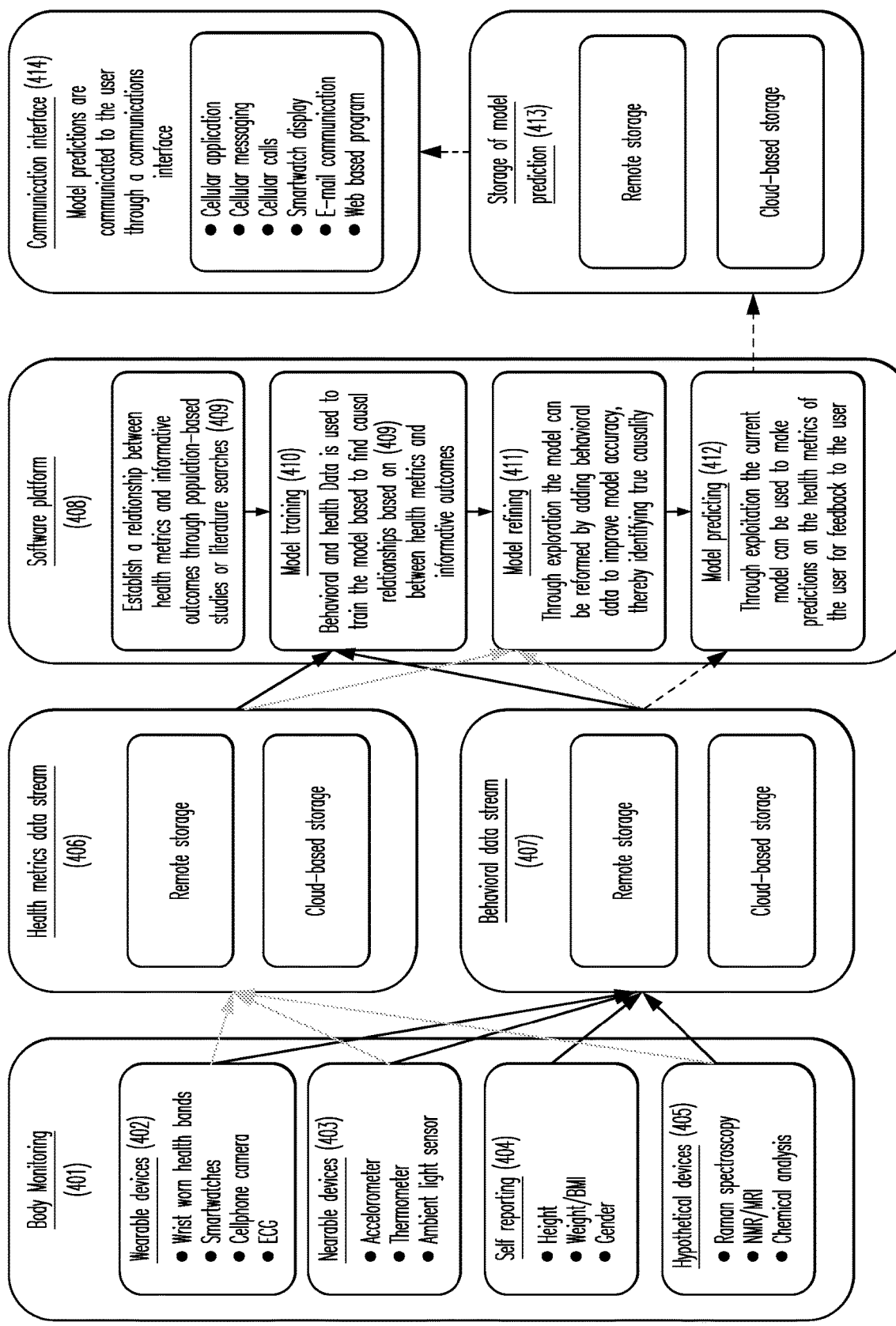
FIG. 4 is an illustration of the system according to an aspect of the invention.

The data streams collected via body monitoring may be transformed into and represented as one or more health metrics and/or behavioral factors by analytics services, which may be internal or external to the digital health platform, as illustrated in FIG. 4. Data collected through body monitoring (401) may be obtained through the use of wearable devices (402) including, but not limited to wrist worn health bands and smartwatches containing PPG, electrodermal activity (EDA), galvanic skin response (GSR) and motion sensors, cell phone cameras and electrocardiogram (ECG) devices worn on the body, and/or the use of nearable devices (403) such as, but not limited to accelerometers, thermometers and ambient light sensors and/or through self-reporting (404) data such as, but not limited to, height, weight, body mass index (BMI), age and gender via methods such as, but not limited to, verbal communication or entering the data into a app-based or web-based platform. In an aspect, the collection of body monitoring data also extends to hypothetical devices (405) that may exist in future such as, but not limited to Raman spectroscopic devices, NMR devices, MRI devices and chemical analytics devices. The data collected through body monitoring may be divided into two data streams, namely health metrics (406) and behavioral data (407), which may be collected through body monitoring and the data stored either remotely making use of storage devices such as, but not limited to portable storage drives, external hard drives and/or internal hard drives on a personal computer or cell phone, or by storing health metric data on a cloud-based storage program such as, but not limited to Google Drive and Amazon Web Service (AWS).

A software platform is used for construction, improvement and training of models that identify and quantify the causal intra-individual relationships between behavioral factors and health metrics and for making model predictions. In an aspect, the software platform is used for the operation of the invention and may be carried out on software compatible services including but not limited to computing on wearable devices, remote computing or cloud based computing. In an aspect, feedback to the user may be done through communication interfaces such as, but not limited to cellular applications, cellular messaging, cellular calls, smartwatch display, e-mail communication and/or web-based programs. The disclosure may refer to the system which encompasses data collection through means including, but not limited to body monitoring, data storage, modeling on software platforms and communicating feedback to the user and is enabled by the IOT setup. In an aspect, the impact of the system may in itself have a causative contribution to the health of the user through user feedback, which may be included into the system as behaviors that impact health metrics. These behaviors include, but are not limited to interaction time with IOT devices, utilization of IOT devices or extent of participation in recommended events.

In an aspect, the software platform (408) may be carried out on software compatible services including, but not limited to, computing on wearable devices, remote computing or cloud based computing. A relationship between health metrics and informative outcomes are established either through performing population-based studies or obtaining such studies from published literature (409). For example, the relationship between biological age as an informative outcome and health metrics has been studied by others and knowledge of this relationship between informative outcomes and health metrics may be used in an embodiment of the invention. The behavioral and health metric data streams are used to train a model (410) to establish a causal relationship between the behavioral data and health metrics for the purposes of augmenting/modifying the users behaviors to improve their informative outcomes.

In an aspect, the behavioral data and health metrics obtained through body monitoring may be used to construct and train models for the prediction of health metrics from behavioral data. Longitudinal changes in behavioral factors such as, but not limited to changes in sleep patterns, exercise regime, drug and supplement usage, and dietary regime can be used to train models for predicting future outcomes in an individual's measurable health metrics such as, but not limited to cardiovascular health metrics, Respiratory Health and VO2max. Furthermore, the models constructed and trained to describe these relationships may be trained on each participant in isolation, resulting in a unique solution for the causal relationship between behavioral factors and health metrics. Therefore, the embodiment of the invention establishes an intra-individual relationship between behavioral factors and health metrics.

The modeling techniques that may be used here are well established and known to those skilled in the art and may include, but are not limited to linear regression, logistic regression, least squares fit modeling, decision tree modeling as well as unsupervised and, more typically, supervised machine learning approaches such as, but not limited to, neural networks, support vector machines, and support vector regression. As an example of how such a model may be embodied in the invention, consider a linear regression where the behavioral data linearly influence changes in health metrics. A model may be constructed to quantify this relationship by, for example, using a least squares fit method to find an optimal causal coefficient that relates health metrics to behaviors that can then be used to predict future health metrics from behavioral data.

In an embodiment of the invention, consider using linear regression to establish a causal relationship between behavioral factors. For example, the behavioral factors can include vigorous exercise duration and total sleep time with the health metrics being resting heart rate. In an aspect the resting heart rate health metric can be assigned to y, a one dimensional scalar of values $y_t$, representing measurements and/or estimates made through continuous body monitoring over time, where t refers to the day of measurement and/or estimation and $y_t$ refers to the mean resting heart rate measured and/or estimated for each day resulting in the scalar y. For instance, mean heart rate three days ago, two days ago, and yesterday may be represented by $y_{-3}$, $y_{-2}$, $y_{-1}$ and today's mean heart rate may be represented by $y_0$.

Furthermore, behavioral factors such as, but not limited to, vigorous exercise duration and total sleep time of values $X_{i,t}$, representing measurements and/or estimates made through body monitoring and/or through manual input are assigned to matrix X, where i refers to the behavioral factor and t refers to the day of measurement. In an aspect, the linear regression model can be trained by using a least squares approximation method.

In short, an adjustable causal coefficient is assigned to each behavioral factor. These coefficients are then optimized by setting $y_t = c_0 + c_1 X_{1,t-1} + c_2 X_{2,t-1} + c_3 X_{3,t-1} + \ldots$ over the range of t. The causal coefficients ($c_0$, $c_1$, $c_2$, $c_3$, ...) that result in the best approximation of the health metric (y) are then returned and can be used to make future predictions of $y_0$.

It should be noted that there may be a time offset between the behavioral factors and the health metric. In the example given above, there is a one-day offset between the behavioral factors (measured and/or estimated on day t−1) and the health metric (measured and/or estimated on day t). In an aspect, the accuracy of the best approximation, also referred to as the $R^2$ value (coefficient of determination), is represented by a value between 0 and 1, where 0 indicates that no relationship exists and where 1 indicates that the values of y can be predicted perfectly from the behavioral factors. The $R^2$ value is one of the common outcomes when training a linear regression model The coefficient of determination is calculated together with a significance value or p-value, which indicates the probability for the coefficient of zero being zero, i.e. the probability that no relationship exists between X and y. A low p-value indicates a small probability for no relationship to exist, typically with a cutoff of 0.05 (1 in 20 chance of the result being spurious) and this measure of statistical significance forms the criteria for making use of a causal relationship between X and y.

In an aspect, it may be required to aggregate behavioral data and/or health metrics measured over several days into a single time window. Over short timescales, the noise present in measurements may make it difficult to obtain information about causal relationships between behavioral factors and health metrics. Using larger timescales of aggregated behavioral data and/or health metrics may aid in reducing the noise to reveal the causal relationships. In the above mentioned example, the behavioral data and health metrics were aggregated over the timeframe of a day. However, a similar modeling approach may be used for larger time aggregation windows. For instance, by calculating the mean resting heart rate over the timeframe of a calendar week and calculating the total vigorous exercise duration and the mean total sleep time over the timeframe of a calendar week, the day-to-day noise becomes less relevant so that better inferences about the causality between the behavior and the health metric may be drawn. Within this exemplary embodiment, the total vigorous exercise duration and mean total sleep time of this calendar week may be used for predicting the mean resting heart rate of the next calendar week.

In an aspect, model training and predicting of outcomes are separated in time from the measurement of the behavioral factors to effectively identify the causal impact that the behavioral factors may have on the health metrics. The continuous collection of the behavioral data and health metrics into longitudinal data streams, may offer the ability to identify causal relationships between the behavioral data and health metrics. For instance, if a causal relationship exists between behavior A (cause) and health metric B (effect), then past values of A should contain information that may aid in predicting B, beyond the historic information contained in values of B alone.

As an example of this consider how a user's resting heart rate during sleep may be predicted from historic data of their sleep resting heart rate. Then it may be considered how vigorous exercise influences the user's resting heart rate during sleep by evaluating whether addition of this variable improves the accuracy in predicting sleep resting heart rate. If improved accuracy is obtained, then this will suggest a causal relationship between vigorous exercise and sleep resting heart rate. This notion of causality is in line with the definition of 'Granger causality'. In an exemplary embodiment of the invention an autoregressive modeling approach with Granger causality may be utilized. For instance, a time series of data may be obtained from measuring the mean resting heart rate during sleep using, for instance, a wearable device, and taking the mean sleep resting heart rate for each day. The time series denoting the mean sleep resting heart rate for every day may be described by a one dimensional scalar noted as y (e.g., $y_{-3}$, $y_{-2}$, $y_{-1}$ as noted above).

Furthermore, a time series of data may be obtained through measuring the vigorous duration performed during exercise events every day noted as $x_t$ and described by a one dimensional scalar noted as x (e.g., $x_{-3}$, $x_{-2}$, $x_{-1}$) with subscript t denoting the day of measurement. The first step would be to establish an autoregressive model where historic values of y are used to predict future values of y. In this example an univariate autoregressive function may be considered where the function may be written as shown in Equation 1 (below) and values of y, between the historic timepoints of τ and T, which is used to train and predict $y_t$. This results in autoregressive coefficients ($a_\tau$, $a_{\tau+1}$, $a_{\tau+2}$, $a_{\tau+3}$, ..., $a_T$) that relate historic values of mean sleep resting heart rate to the current value of mean sleep resting heart rate and an error value e(t) for every t that gives the difference between the measured and/or estimated mean sleep resting heart rate and the calculated mean sleep resting heart rate for each day using historic values.

$$y(t) = \sum_{\tau=1}^{T} (A_\tau \cdot y(t-\tau)) + e(t) \quad \text{Eq. 1}$$

Next, a bivariate autoregressive model may be constructed for evaluating the contribution that x (vigorous exercise duration) may have on the predictability of $y_t$. This is done by introducing lagged values of x into the autoregressive model and thus the model may be written as shown in Equation 2 (below). In Equation 2, the autoregressive coefficients ($a_\tau$, $a_{\tau+1}$, $a_{\tau+2}$, $a_{\tau+3}$, ..., $a_T$) relate historic values of y to $y_t$; the autoregressive coefficients ($b_\tau$, $b_{\tau+1}$, $b_{\tau+2}$, $b_{\tau+3}$, ..., $b_T$) relate historic values of x to $y_t$; and the error value ε(t) for every t gives the difference between the measured and/or estimated $y_t$ and the calculated $y_t$ for each day using historic values of y and x. To evaluate whether the behavioral scalar x (vigorous exercise duration) has a Granger causal relationship with health scalar y (mean sleep resting heart rate) a Granger causality test may be performed.

$$y(t) = \sum_{\tau=1}^{T} (A_\tau \cdot y(t-\tau)) + \sum_{\tau=1}^{T} (B_\tau \cdot y(t-\tau)) + \varepsilon(t) \quad \text{Eq. 2}$$

The value of $y_t$ using the univariate model is calculated using historical data of y between timepoints τ and T and compared to the measured and/or estimated value of $y_t$. This results in a value e (the univariate error) for every timepoint (t) that is the difference between the predicted and measured and/or estimated value of $y_t$. Similarly, the value of $y_t$ using the bivariate model is calculated using historical data of y and x between timepoints r and T and compared to the measured and/or estimated value of $y_t$. This results in a value a (the bivariate error) for every timepoint(t) that is the difference between the predicted and measured and/or estimated value of $y_t$. The Granger causality test relies on the difference in the variance of the univariate error e and the variance of bivariate error a to determine whether there is a Granger causal relationship between x and y. This is done through the use of Equation 3:

$$GC = \log \frac{\text{Var}[e_t]}{\text{Var}[\varepsilon_t]} \quad \text{Eq. 3}$$

Evaluation of Equation 3 will suggest that if no causal relationship exists between x and y then the variance in $e_t$ and the variance in $\varepsilon_t$ would be equal to each other, resulting in an GC outcome of 0. Whereas if a causal relationship exists between x and y, the variance in $e_t$ will be greater than the variance in $\varepsilon_t$, resulting in a GC outcome that is a positive number. Furthermore, the greater the Granger causal relationship between x and y, the larger the GC outcome will be. It may be concluded that x Granger causes y when a GC value is larger than a specific threshold value which may be arbitrarily selected. A value larger than the GC threshold may therefore suggest, for the purposes of this disclosure, that there exists a causal relationship between the behavioral data (x) and the health metric (y). A similar approach could be employed to evaluate all of the behavioral factors available for a user to identify behaviors that cause changes in the health metric of interest. Within this exemplary embodiment of the invention, it may be concluded that vigorous exercise duration and total sleep time has a causal relationship with mean resting heart rate. Therefore, the Granger causality test may be used to identify behaviors that cause changes in a given health metric.

Improving the Data

In an aspect, the invention uses machine learning methods such as, but not limited to, the Granger causality test, as discussed in the exemplary embodiment of the invention above, to identify causality between behavioral factors and health metrics by determining which behavioral factors have a significant impact on specific health metrics, and implement these causal relationships to improve models for predicting health metrics. However, the ability of the system to identify causal relationships relies on the availability of sufficient data in the behavioral and health data streams. In an aspect, the invention may use reinforced machine learning methods, such as, but not limited to, Q-learning, which has the ability to request that the user perform specific (randomized) behaviors, with regards to the time of day, intensity and duration of the behavior, for the purpose of refining the causal relationship model.

In an embodiment of the invention, a reinforced learning approach (e.g., Q-learning) may be used to influence the user's behaviors for the generation of new behavioral and health data for refining the intra-individual causal models. In an aspect, the impact that total sleep time and the vigorous duration during exercise events (behavioral input) have on an individual's mean resting heart rate (S) may be evaluated. Here the state ($A_t$) of each timestep (t) may refer to the duration of vigorous exercise events and total sleep time, and the size of the timestep (t) may refer to one calendar week. In an aspect, the A and the S of the user would be measured and/or estimated for each timestep. The A of the current timestep ($A_t$) may then be used to predict the $S_{t+1}$ of the following timestep (t+1) as laid out in the linear regression example above. Evaluation of the impact of A on the health of the user is achieved through a specific reward value (R) calculated as the difference in S between consecutive timepoints.

Deriving a reward value for the Q-learning aspect of the present invention relies on the establishment of criteria for evaluating the impact of behavioral factors on health metrics through the prior establishment of relationships between health metrics and informative outcomes. Prior establishment of these relationships may be obtained through conducting population-based studies such as, but not limited to, correlations between smoking status as a health metric and life expectancy as an informative outcome, breathing volume as a health metric and the risk of developing chronic respiratory diseases as an informative outcome, or through established relationships between health metrics and informative outcomes reported in literature focused on studies such as cross-section studies or meta-analysis studies. Regarding the establishment of a reward value through correlating health metrics to informative outcomes, the informative outcomes establish a healthy vs. unhealthy criteria which may be correlated to health metrics. For instance, a longer life expectancy may be preferable to a shorter life expectancy, and since the correlatory relationship between smoking status and life expectancy is established, it therefore entails that not smoking (associated with longer life expectancy) may be preferable to smoking (associated with shorter life expectancy). For the purpose of this exemplary embodiment of the invention a higher reward may be associated with a decrease in mean resting heart rate and therefore that $R=S_{t-1}-S_t$. If the mean resting heart rate decreased during timesteps (t−1) and (t) then R>0 and a positive reward is returned, whereas if the mean resting heart rate increased during timesteps (t−1) and (t) then R<0 and a negative reward is returned.

In an aspect the user can take specific actions (A) at each timestep which would entail changing the total vigorous exercise duration events and their total sleep time during each timestep t. The remainder of setting up the Q-learning algorithm is known in the art and involves the setting of parameters, specifically the learning rate ($\alpha$) and the future discount factor ($\gamma$), as well as the application of the Bellman equation to learn an optimal decision policy for the user (Q) that will tell the user the most rewarding action to take given their current behaviors ($A_t$) and based on having learned Q from historic data.

Another salient and well described aspect known to those skilled in the art and of interest in the embodiment of the invention is that the algorithm has the ability to switch between two primary modes. The first of these modes being exploration, where random actions are recommended to the user in order to learn which S creates an optimal reward. The second mode is exploitation, where the decision policy Q is used without it being changed through learning to perform what is understood to be the optimal action available. A random choice is made in the algorithm between either exploitation or exploration at the start of each timestep (t). This random choice is influenced by the ε-greedy parameter (ε) known to those skilled in the art. The E parameter is a value that is set between the values of 0 and 1, where 1 would represent the algorithm functioning only in exploration mode and 0 would represent the algorithm only functioning in exploitation mode. The ε-greedy parameter is typically set to 1 such that it initially favors exploration, while the ε-greedy parameter typically decays over time to favor exploitation as the decision policy improves, to reap high rewards from an effective policy learned from many data points. The ε-greedy parameter decay function is described in the Q-learning algorithm and would be recalculated for each timestep. Furthermore, a random value is generated for each timestep and compared to the e parameter. If the random value is larger than the ε-greedy parameter, the system will function in exploration mode, whereas if the random value is smaller than the ε-greed parameter, the system will function in exploitation mode. In this approach, the operation of exploration and exploitation means that during the algorithm functioning in explorative mode, the user will receive a randomized behavior composition recommendation regarding vigorous duration during exercise events and total sleep time, to generate new data for improving the decision policy (Q).

When a well trained Q is obtained and c allows for exploitation mode, the user will get more consistent recommendations. The process of discovering the optimal decision policy (Q) through data on randomized actions determines and leverages causal links between behavioral choices and changes in health metrics. On the other hand, exploitation may be used to leverage the system's current understanding of the best possible behaviors required to maximize health to make predictions of health metrics using the current model and recommend these behaviors to the user for the health maximum benefit for the user under the current understanding of the causal relationship between behavioral factors and health metrics, as established by the system.

As illustrated in FIG. 4, the model may use exploration mode to recommend randomized behaviors to the user and generate new behavioral and health data streams that may be used for model refining (411). The model may use exploitation mode to use the current understanding of the model to make model predictions (412) of the health metrics of the user. The model predictions may be recorded and the data stored (413) either through remote storage making use of storage devices such as, but not limited to, portable storage drives, external hard drives and/or internal hard drives on a personal computer or cell phone, or by storing health metric data on a cloud-based storage program such as, but not limited to, Google Drive and AWS. In an aspect, the model predictions may then be communicated to the user as feedback, making use of a communication interface (414) such as, but not limited to cellular applications, cellular messaging, cellular calls, smartwatch display, e-mail communication and/or web-based programs.

In an aspect, training of the model and improving on the model through exploration is a continuous process. This continuous process results in an iterative process of data generation (through randomized recommendations in exploration mode), model training (through modeling techniques such as, but not limited to, linear regression), identification of causal relationships (through methods such as, but not limited to, the Granger causality test) and optimization of the decision policy (through methods, such as, but not limited to, Q-learning). Another example process for improving the model is the use of A/B testing, which may comprise requesting behavior modifications to two groups in two different ways, and evaluating which group makes the recommended behavioral modification. This iterative process allows for a dynamic modeling system to operate until an optimal decision policy (Q) has been derived and where the value of e allows for the system to continuously operate in exploitation mode.

In an aspect the feedback given to the user is an important feature of the invention. In an aspect feedback to the user may be done through communication interfaces such as, but not limited to cellular applications, cellular messaging, cellular calls, smartwatch display, e-mail communication and/or web-based programs. The intra-individual causal relationships between behavioral factors and health metrics may be identified and quantified by the system with the explicit aim of informing an individual about the relationship between their existing state of health metrics and behavioral factors or behavioral data. In an aspect, the invention evaluates behavioral factors or behavioral data within a specified user, by identifying and selecting behavioral parameters and modeling the impact of selected behavioral parameters on health metrics and comparing the resulting causal factors to find the optimal decision policy (Q) for augmenting and/or modifying behaviors to give the best predictive accuracy of health metrics, with the purpose of optimizing the health of the specified user. This allows for the development of a behavior management system that may be communicated through to the user for optimizing the health of the user. Furthermore, The application of the invention may aim to function as a personal trainer operating on the IOT setup that may recommend behavioral conduct aimed at optimizing the health of the individual.

For example, the IOT setup can be that as illustrated in FIG. 5. In an aspect, the invention may use mobile devices (501) such as, but not limited to, cell phones for the purpose of inputting behavioral data (502) such as, but not limited to, the initiation or completion of fitness and sleep events, as well as for inputting health metrics (503) such as, but not limited to, height, weight, age, gender and skinfold measurement. Furthermore, mobile devices (501) may be used for remote storage (504) of behavior and health data and as a software platform (505) for modeling causal relationships between behavior and health data. Moreover, mobile devices (501) may act as communication interfaces (506) to deliver feedback to the user or third parties.

Monitoring devices (507) such wearable and nearable devices may be used for the monitoring and recording of behavioral data (508) and health data (509). Monitoring devices (507) may be used for the remote storing of data streams (510) and as a software platform (511) for modeling causal relationships between behavior and health data. Monitoring devices (507) may also function as a communication interface (512) for displaying results and recommendations to users. A cloud based system (513) such as but not limited to, Google Drive or Amazon Web Services (AWS) may be used for cloud based storage (514) of behavioral and health data streams, or as a software platform (515) for modeling causal relationships between behavior and health data. In an aspect, multiple devices and a cloud based system may be used within an embodiment of the invention and these devices will be connected to one another and communicate with one another through the internet (516) allowing for data transfer between devices and the cloud based system as well as employing different modeling steps on different software platforms.

The behavioral conduct recommended by the invention (personal trainer) may be in the form of random recommendations when the system operates in exploration mode, or may be in the form of recommending the optimal decision policy (Q) to the user, when operating in exploitation mode. Moreover, the causal relationships derived from larger time windows of behavioral factors and health metrics may be extrapolated to arrive at the causal effects expected for smaller time units of behaviors and that the purpose of this is to provide instant gratification, which is an important component of successful behavioral intervention. For instance, consider that the system establishes a causal relationship between exercise performed within the period of a week (7-day aggregation window) and mean resting heart rate after recovery from the exercise event, the system may then extrapolate the established causal relationship based on performed exercise events in order to make predictions on resting heart rate as soon as the exercise event has been concluded for instantaneous feedback to the user. The more instantaneous the feedback, the more likely the user is to change their behaviors, since the cause and effect relationship is more relatable at the instance of completing the behavior. Extrapolation of the causal relationship may be done with different degrees of modeling sophistication ranging from simply assuming additivity of behavior towards cause. or instance, every exercise event has a compounding effect on resting heart rate predictions to much more sophisticated time series models, or in another instance, where every exercise event's impact on resting heart rate decreases as the time difference between the exercise event and the day of prediction increases.

Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. Thus, it is impossible for any program to damage the execution of any of the other programs running on the system. However, the programs have no way to exchange any information except through the operating system (or by reading files stored on the file system).

Multi-process computing is similar to multi-tasking computing, as the terms task and process are often used interchangeably, although some operating systems make a distinction between the two. The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire. Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s).

In some alternative implementations, the functions noted in the blocks may occur out of the order noted in the Figures. For example, two blocks shown in succession may, in fact, be executed substantially concurrently, or in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or that carry out combinations of special purpose hardware and computer instructions. Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

From the above description, it can be seen that the present invention provides a system, computer program product, and method for the efficient execution of the described techniques. References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. § section 112, sixth paragraph, unless the element is expressly recited using the phrase "means for" or "step for."

While the foregoing written description of the invention enables one of ordinary skill to make and use what is considered presently to be the best mode thereof, those of ordinary skill will understand and appreciate the existence of alternatives, adaptations, variations, combinations, and equivalents of the specific embodiment, method, and examples herein. Those skilled in the art will appreciate that the within disclosures are exemplary only and that various modifications may be made within the scope of the present invention. In addition, while a particular feature of the teachings may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising."

Other embodiments of the teachings will be apparent to those skilled in the art from consideration of the specification and practice of the teachings disclosed herein. The invention should therefore not be limited by the described embodiment, method, and examples, but by all embodiments and methods within the scope and spirit of the invention. Accordingly, the present invention is not limited to the specific embodiments as illustrated herein, but is only limited by the following claims.

What is claimed is:

1. A method for improved health management using an IoT setup of interconnected electronic devices and sensors, the method comprising:
   measuring and storing behavioral data and health data of a plurality of users;
   analyzing the health data of the plurality of users to establish informative outcomes;
   generating health metrics from the health data;
   establishing a relationship between the informative outcomes and the health metrics;
   identifying and quantifying a causal relationship between the behavioral data and the health data from a behavior time window and from a health data time window, wherein the beginning of the behavior time window precedes the beginning of the health data time window, to derive behavioral recommendations, wherein a causal relationship between the behavioral data and the health data is established by:
   (a) using machine learning to derive models to describe the causal relationship between the behavioral data and the health data;
   (b) communicating the causal relationship between the behavioral data and the health data to the user for the purpose of illustrating the impact of their behaviors on their health;
   (c) calculating optimal behavioral changes through deriving an optimal decision policy and recommending changes to the user's behavior either through making randomized changes to behaviors when operating in exploration mode, or through recommending the changes in behavior based on the current decision policy when operating in exploitation mode;
   (d) using reinforcement learning techniques to evaluate whether the behavior feedback to the user is randomized for the purpose of generating more data for learning, or whether the behavior feedback to the user is optimal to improve the health of the user, wherein the reinforcement learning techniques comprise Q-learning and ε switching which are used to control when the exploration and the exploitation are performed by the system, wherein the exploration comprises learning through randomized changes in recommended behavior and the exploitation comprises applying an optimized decision policy, wherein operating in the exploration mode occurs when an ε-greedy parameter is greater than or equal to a predefined threshold, operating in the exploration mode, and when the ε-greedy parameter is lesser than a predefined threshold, operating in the exploitation mode; and
   (e) motivating the user to modify the user's behaviors for the purpose of improving the user's health and well-being;
   providing the derived behavioral recommendations to one of the plurality of users or to a third party; and investigating changes to the information that was sent to the third party to influence user behavior optimally.

2. The method of claim 1, wherein the behavioral data comprises at least one of:
sleep parameters comprising total sleep time, bedtime variability or wake-up time variability,
exercise parameters comprising intensity minutes, event duration and event type,
dietary regime comprising amounts of proteins, fats, carbohydrates and fiber, or
medication usage such as glucose management, blood pressure medication or antidepressant use.

3. The method of claim 1, wherein the health data comprises at least one of:
cardiovascular metrics comprising resting heart rate, pulse waveform, heart rate variability or pulse wave velocity,
respiratory metrics comprising resting breathing rate, breathing volume or cough frequency; or
oxygen saturation comprising VO2max measurements.

4. The method of claim 1, wherein the informative outcomes comprises:
vitality comprising risk of all cause mortality, risk of developing cardiovascular diseases, life expectancy, biological age or years left to live;
respiratory health comprising risk of developing chronic respiratory diseases; or
fitness level comprising fitness scoring and recovery time after fitness events.

5. The method of claim 1, wherein the behavioral data are measured by sensors, wherein the sensors comprise accelerometers, inertial gyroscopes, stop-motion sensors, or Micro Electro Mechanical Systems (MEMS) embedded in wearable devices or nearable devices.

6. The method of claim 1, wherein the health metrics are measured using physiological signal sensors comprising heart rate sensors, PPG sensors, oximetry sensors, electrodermal activity (EDA), galvanic skin response (GSR), or ECG sensors embedded in wearable or nearable devices.

7. The method of claim 1, wherein the IOT setup stores the behavior data and the health data remotely from the user.

8. The method of claim 1, wherein the machine learning comprises using linear regression, logistic regression, least squares fit modeling, decision tree modeling, unsupervised machine learning, or supervised machine learning approaches to model the causal relationship between the behavioral data and the health data.

9. The method of claim 1, wherein data within a specific time window size is used to discover causative or potentially causative relationships between behavioral factors and health metrics and where those relationships are then extrapolated to smaller time durations, such as a single day, to provide increasingly more immediate feedback to the user, for the purpose of effecting behavioral change as the cause and effect relationship is still fresh in the mind of the user.

10. The method of claim 1, wherein the time window of behavioral data and the time window of health data comprise adjacent and non-overlapping time windows or comprise limited-overlapping time windows, and wherein the behavioral data and the health data are used to discover causative relationships between behavioral factors and health metrics where the start of the behavioral data time window precedes the start of the health data time window and where a causal relationship comprises utilizing a Granger causality test.

11. The method of claim 1, wherein deriving recommendations comprises Q-learning to derive an optimal decision policy of recommendations of behaviors for feedback to the user.

12. The method of claim 1, wherein the e-greedy parameter switching depends on the accuracy of the model describing the causal relationship between behavioral and health data, wherein the model will operate more in exploration mode if a statistically significant causal relationship is not obtained, and the model will operate more in exploitation mode if a statistically significant causal relationship is obtained.

13. The method of claim 1, further comprising requesting the user to perform behavioral changes, which may further comprise manual confirmation, or which may further comprise automatic detection in the behavioral data, and which are randomized when operating in exploration mode, and which are based on an optimized decision policy, when operating in exploitation mode.

14. The method of claim 1, wherein the relationship between the behavioral data and the health data is tested and refined by randomizing the behavior recommendations made by the method and, wherein an effect of this randomization is monitored statistically to improve the model.

15. The method of claim 1, wherein the feedback is provided to the user via a user communication interface comprising a smart watch display, cellular applications, cellular messaging, cellular calls or web-based programs.

16. The method of claim 15, wherein the feedback may include recommendations of behaviors for the user to complete including daily or weekly goals, and wherein the recommended behaviors are those behaviors with the largest causal relationship between behavioral data and health data.

17. The method of claim 1, wherein changes to a behavioral program are made such as to omit or reduce recommendations on behavior as well as feedback to the user to quantify the overall causal effect of the IOT intervention system in bringing about changes in health metrics, and wherein the data may be aggregated over multiple users to prove causal effects on health by introducing the system to a population.

18. The method of claim 17, wherein the behavioral suggestion changes may be reduced or removed for the purposes of AB testing, or within a control group to evaluate quantitatively the impact of the system as a whole on population health.

19. The method of claim 1, further comprising investigating changes to the information that was sent to third parties to influence end-user behavior optimally.

* * * * *